US008410315B2

(12) United States Patent
Limbach et al.

(10) Patent No.: US 8,410,315 B2
(45) Date of Patent: Apr. 2, 2013

(54) METHOD FOR PRODUCING OLEFINICALLY UNSATURATED CARBONYL COMPOUNDS BY OXIDATIVE DEHYDROGENATION OF ALCOHOLS

(75) Inventors: Michael Limbach, Worms (DE); Joaquim Henrique Teles, Otterstadt (DE); Radwan Abdallah, Ludwigshafen (DE); Torsten Mäurer, Lambsheim (DE); Thorsten Johann, Limburgerhof (DE)

(73) Assignee: BASF SE (DE)

( * ) Notice: Subject to any disclaimer, the term of this patent is extended or adjusted under 35 U.S.C. 154(b) by 169 days.

(21) Appl. No.: 12/920,139

(22) PCT Filed: Feb. 27, 2009

(86) PCT No.: PCT/EP2009/052383
§ 371 (c)(1),
(2), (4) Date: Aug. 30, 2010

(87) PCT Pub. No.: WO2009/106621
PCT Pub. Date: Sep. 3, 2009

(65) Prior Publication Data
US 2011/0004025 A1 Jan. 6, 2011

(30) Foreign Application Priority Data
Feb. 28, 2008 (DE) .................. 10 2008 011 767

(51) Int. Cl.
*C07C 45/38* (2006.01)
(52) U.S. Cl. .................. 568/471; 568/473; 568/489
(58) Field of Classification Search .................. 568/471, 568/473, 489
See application file for complete search history.

(56) References Cited

U.S. PATENT DOCUMENTS

| | | | |
|---|---|---|---|
| 3,156,735 A * | 11/1964 | Armstrong | 585/624 |
| 3,697,580 A | 10/1972 | Overwien et al. | |
| 4,007,135 A | 2/1977 | Hayden et al. | |
| 4,110,403 A | 8/1978 | Ichikawa et al. | |
| 4,117,016 A | 9/1978 | Hughes | |
| 4,154,762 A | 5/1979 | Huang et al. | |
| 4,165,342 A | 8/1979 | Dudeck et al. | |
| 4,310,709 A | 1/1982 | Rebafka | |
| 4,324,699 A | 4/1982 | Mross et al. | |
| 4,732,918 A | 3/1988 | Lohmueller et al. | |
| 5,149,884 A | 9/1992 | Brenner et al. | |
| 6,013,843 A | 1/2000 | Aquila et al. | |
| 6,211,114 B1 | 4/2001 | Brocker et al. | |
| 2006/0036106 A1 | 2/2006 | Mazanec et al. | |

FOREIGN PATENT DOCUMENTS

| | | |
|---|---|---|
| DE | 1901709 | 8/1970 |
| DE | 2020865 A1 | 11/1971 |
| DE | 2041976 A1 | 3/1972 |
| DE | 2300512 | 7/1973 |
| DE | 2454972 | 6/1975 |
| DE | 2521906 | 12/1975 |
| DE | 2517859 | 3/1976 |
| DE | 2517859 A1 | 3/1976 |
| DE | 2715209 | 10/1978 |
| DE | 2751766 | 5/1979 |
| DE | 2753359 | 6/1979 |
| DE | 3414717 A1 | 10/1985 |
| EP | 0011356 | 5/1980 |
| EP | 0014457 | 8/1980 |
| EP | 0082609 | 6/1983 |
| EP | 0085237 A1 | 8/1983 |
| EP | 0112261 | 6/1984 |
| EP | 0112261 A1 | 6/1984 |
| EP | 0172565 A2 | 2/1986 |
| EP | 244632 A2 | 11/1987 |
| EP | 0266015 A1 | 5/1988 |
| EP | 0339748 A2 | 11/1989 |
| EP | 357292 A1 | 3/1990 |
| EP | 0357293 A1 | 3/1990 |
| EP | 0415745 A2 | 3/1991 |
| EP | 841090 A2 | 5/1998 |
| EP | 881206 A1 | 12/1998 |
| EP | 0881206 A1 | 12/1998 |
| GB | 1338698 A | 11/1973 |
| GB | 1413251 | 11/1975 |
| GB | 1512625 | 6/1978 |
| JP | 59-112937 A | 6/1984 |
| JP | 8268939 A | 10/1996 |
| WO | WO-01/96324 A2 | 12/2001 |
| WO | WO-02/18042 A1 | 3/2002 |
| WO | WO-03/044003 A1 | 5/2003 |
| WO | WO-2004/002971 A1 | 1/2004 |
| WO | WO-2004/030813 A1 | 4/2004 |
| WO | WO-2008/037693 A2 | 4/2008 |
| WO | WO-2008/098774 | 8/2008 |

OTHER PUBLICATIONS

Abad, A., et al., "Unique gold chemoselectivity for th eaerobic oxidation of allylic alcohols," Chem., Commun. 2006., pp. 3178-3180.
Abad, A., et al., "Catalyst parameters determining activity and selectivity of supported gold nanoparticles for the aerobic oxidation of alcohols: the molecular reaction mechanisn," Chem. Eur. J. 2008, vol. 14, pp. 212-222.
U.S. Appl. No. 12/297,895, filed Oct. 21, 2008, Maurer et al.
U.S. Appl. No. 12/920,150, filed Aug. 30, 2010, Brenner et al.

(Continued)

*Primary Examiner* — Sikarl Witherspoon
(74) *Attorney, Agent, or Firm* — Novak Druce Connolly Bove + Quigg LLP

(57) ABSTRACT

A process for preparing olefinically unsaturated carbonyl compounds by oxidative dehydrogenation in an oxygenous atmosphere over a supported catalyst which comprises gold and optionally further noble metals at temperatures in the range from 50 to 240° C.

13 Claims, No Drawings

OTHER PUBLICATIONS

U.S. Appl. No. 12/933,441, filed Sep. 20, 2010, Maurer et al.

Kestenbaum, H., "Zur synhese von ethenoxid in einem mikroreaktionssystem," 2004, Dissertationsschrift, Frankfurt, Main, DE.

"Microreactors," Ullmann's Encyclopedia of Industrial Chemistry, Wiley-VCH, Weinheim, DE, 2002, vol. 22, pp. 1-29.

Ullmann's Encyclopedia of Industrial Chemistry (5th Ed.), VCH Verlagsgesellschaft, Weinheim, 1987, vol. A10, pp. 117-135.

* cited by examiner

METHOD FOR PRODUCING OLEFINICALLY UNSATURATED CARBONYL COMPOUNDS BY OXIDATIVE DEHYDROGENATION OF ALCOHOLS

CROSS-REFERENCE TO RELATED APPLICATIONS

This application is a national stage application (under 35 U.S.C. §371) of PCT/EP2009/052383, filed Feb. 27, 2009, which claims benefit of German application 10 2008 011 767.6, filed Feb. 28, 2008.

BACKGROUND OF THE INVENTION

The present invention relates to a process for preparing olefinically unsaturated carbonyl compounds by oxidative dehydrogenation of alcohols in an oxygenous atmosphere over a supported catalyst.

The oxidative dehydrogenation of unsaturated alcohols to aldehydes is known per se and is described in the literature.

DE-A-25 17 859 describes the dehydrogenation of unsaturated alcohols over copper catalysts, which is performed essentially in the absence of oxygen. This forms mixtures of different aldehydes which have to be separated into the components thereof in complex separating operations if pure products are desired.

DE-B 20 20 865 and DE-B-20 41 976 describe the dehydrogenation of β,γ-unsaturated alcohols or α,β-unsaturated alcohols to α,β-unsaturated aldehydes at temperatures in the range from 150 to 600° C. The dehydrogenation catalysts mentioned include mixed catalysts, for example those composed of copper and silver. A disadvantage is that considerable amounts of nucleophilic substances have to be added.

U.S. Pat. No. 4,154,762 describes a process for preparing aldehydes and ketones, by which the corresponding alcohols are converted at temperatures in the range from 250 to 600° C. in the presence of a gold catalyst. This process uses a solid gold catalyst, which is therefore correspondingly expensive.

EP-A-244 632 describes a tube bundle reactor for performance of catalytic organic reactions in the gas phase, which is characterized by particular dimensions of the reaction tube lengths relative to the internal diameter. The oxidative dehydrogenation is performed at temperatures in the range from 300 to 600° C. over a supported catalyst.

EP-A-881 206 describes a process for continuous industrial preparation of unsaturated aliphatic aldehydes in a tube bundle reactor, in which the actual reaction is preceded by passing the reaction mixture through the supported catalyst above the dew point of the alcohol used but below the start temperature of the reaction. The actual oxidative dehydrogenation in the process described in this document also takes place at temperatures of 300° C. or more.

Angew. Chem. Int. Ed. 2007, 47, pages 138-141 describes oxidizing agent-free alcohol dehydrogenation using a recyclable supported silver catalyst on a hydrotalcite support. The reaction is performed in the absence of oxygen, for is example in an argon atmosphere. According to example 16 in Tab. 1, an olefinically unsaturated alcohol with a phenyl substituent is converted to the corresponding aldehyde in the absence of oxygen.

BRIEF SUMMARY OF THE INVENTION

The present invention provides a process for preparing olefinically unsaturated carbonyl compounds of the general formula I

where $R^1$ is hydrogen when $R^2$ is a radical of the general formula II

or $R^1$ and $R^2$ together are a radical of the general formula III

and $R^3$, $R^4$, $R^5$ and $R^6$ may each independently be hydrogen, a $C_1$-$C_{18}$ alkyl group, an optionally substituted $C_5$-$C_{18}$-cycloalkyl group or an optionally substituted $C_6$-$C_{18}$-aryl group, where some of the ring atoms of the cycloalkyl and aryl groups may be replaced by heteroatoms selected from N, O and S, by oxidative dehydrogenation of alcohols of the general formula IV in an oxygenous atmosphere

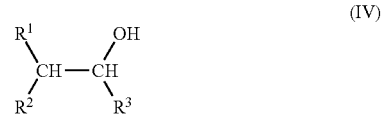

where $R^1$ and $R^2$ may each be as defined above over a gold catalyst, the gold catalyst being supported and comprising gold or mixtures of gold and noble metals selected from Cu, Ag, Pd, Pt, Rh, Ru, W and Os, and the reaction being performed within a temperature range from 50 to 240° C. in the presence of air, hydrogen peroxide or a gas or gas mixture with an oxygen content of 7-30% by volume as the oxygenous atmosphere.

DETAILED DESCRIPTION OF THE INVENTION

Preferred embodiments of the process according to the invention can be inferred from the description which follows and the dependent claims.

In the process according to the invention, it is possible to prepare olefinically unsaturated carbonyl compounds of the general formula I, where $R^1$ in this formula is hydrogen and $R^2$ is a radical of the formula II, or $R^1$ and $R^2$ together are a radical of the general formula III.

The substituents $R^3$, $R^4$, $R^5$ and $R^6$ in the general formulae I to III are each independently hydrogen, a $C_1$-$C_{18}$ alkyl group, an optionally substituted $C_5$-$C_{18}$ cycloalkyl group or an optionally substituted $C_6$-$C_{18}$ aryl group. Preferred substituents on the cycloalkyl or aryl groups include $C_1$-$C_6$ alkyl radicals or $C_1$-$C_6$ alkoxy radicals. Examples of alcohols of the general formula IV include 3-butene-1-ol, 3-pentene-1-ol, 3-methylbut-3-en-1-ol, 3-methylbut-2-en-1-ol, 1-pentene-4- ol, 3-hexene-1-ol, 3-methylpent-3-en-1-ol, 3-ethylbut-3-en-1-ol, 2-methylhex-1-en-5-ol, 2-methylhex-1-en-4-ol, 2-phenylbut-1-en-4-ol, 4-methylpent-3-en-1-ol and 2-cyclohexylbut-1-en-4-ol. A particularly preferred alcohol of the formula IV is 3-methylbut-3-en-1-ol, also known by the trivial name isoprenol. It is also possible with preference to use 3-methylbut-2-en-1-ol, known to the person skilled in the art by the trivial name of prenol.

The alcohols of the formula IV are known and the preparation thereof has been described in the literature.

In the process according to the invention, it is possible to use mixtures of different alcohols of the formula IV or the corresponding pure alcohols as starting compounds.

It has been found to be advantageous to use mixtures of 3-methylbut-3-en-1-ol (isoprenol) and 3-methylbut-2-en-1-ol (prenol). It is possible in principle to use any desired mixing ratio of these alcohols; a particularly good ratio with regard to maximum prenal selectivities has been found to be a ratio of 1:1 to 1:2 (isoprenol/prenol, mol/mol). In the case of use of pure isoprenol, prenol or other mixing ratios thereof with one another, the ratio of about 1:2 mentioned (isoprenol/prenol, mol/mol) is in some cases established at first under oxidative conditions. The preferred substrate for the oxidation reaction which then sets in is not isoprenol, as would be expected according to the prior art, but prenol itself, which is formed under some circumstances by isomerization. This is observed especially in the case of use of supports based on carbon.

According to the invention, the oxidative dehydrogenation is performed at temperatures in the range from 50 to 240° C., preferably in the range from 100 to 200° C. and more preferably in the range from 100 to 150° C. In the literature, oxidative dehydrogenations of corresponding alcohols are generally performed at temperatures of above 300° C. (cf. EP-A 244 632 and EP-A 881 206), which harbors the risk of side reactions and decomposition of the reactants and also of the desired reaction products, owing to these high reaction temperatures. In comparison, the lower temperatures in the process according to the invention constitute a considerable and technically relevant advantage.

According to the invention, the conversion is performed in an oxygenous atmosphere, i.e. with an oxygen-comprising gas as an oxidizing agent. The corresponding oxidizing agents used may be gases or gas mixtures with an oxygen content in the range of 7-30% by volume, preferably of 9-18% by volume. It is also possible to use air, being a readily available oxidation medium. Alternatively, hydrogen peroxide is also suitable as an oxidizing agent.

According to the invention, the supported catalyst used, i.e. the catalyst applied to a support, is a gold-comprising supported catalyst or a corresponding catalyst which, in addition to gold, may comprise a further noble metal selected from Cu, Ag, Pd, Pt, Rh, Ru, W or Os. The use of gold or mixtures of gold and other noble metals allows the oxidative dehydrogenation to be performed at significantly lower temperatures than those described to date in the prior art. Especially in the case of the preferred preparation of 3-methylbut-2-en-1-al, it is possible to achieve reaction temperatures below 150° C., which is advantageous for the product quality and suppresses undesired side reactions.

The molar ratio of gold to the other noble metals is not subject to any particular restriction and can be selected freely.

In the case of use of 3-methylbut-3-en-1-ol (isoprenol) as the alcohol of the formula IV, the use of supported catalysts which, as well as gold, comprise a noble metal selected from Pd, Pt and Ru has been found to be useful. These supported catalysts catalyze the isomerization of isoprenol to prenol (3-methylbut-2-en-1-ol), which can then be converted to 3-methylbut-2-en-1-al without requiring a downstream isomerization step (of 3-methylbut-3-en-1-al to 3-methylbut-2-en-1-al).

The noble metal content of the supported catalysts which are used in the process according to the invention is not subject to any particular restriction per se and may be in the range from 0.1 to 10% by weight, preferably in the range from 0.4 to 5% by weight and more preferably in the range from 0.6 to 3% by weight.

Suitable support materials for the catalyst are the support materials for such catalysts which have been described in the literature and are known per se to those skilled in the art. Merely by way of example, mention should be made here of aluminum oxide, silicon dioxide, magnesium oxide, silicon carbide, steatite or hydrotalcite. Suitable support materials in principle are basic, acidic or else amphoteric support materials, and basic materials have been found to be particularly suitable in some cases. Aluminum oxides, basic aluminosilicates or hydrotalcites especially aluminum oxides and hydrotalcites, have been found to be advantageous in some cases. Support materials based on carbon, for example various kinds of charcoal, are also suitable.

Processes for preparing suitable support materials are likewise known per se to those skilled in the art and are described in the literature. Merely by way of example, reference is made here, for the preparation of hydrotalcites as support materials, to Cavani et al., *Catal. Today*, 1991, 11, pages 173ff.

Hydrotalcite is generally understood to mean a layer material with the chemical formula $[M(II)_{1-x}M(III)_x(OH)_2]^{x+}[A_{n/x}]^{n-} \times m\ H_2O$. M(II) therein is a divalent metal, M(III) a trivalent metal, A is an anion intercalated in the lattice, m is the number of intercalated water molecules and x is the molar ratio M(II)/[M(II)+M(III)]. Typically, x is in the range from 0.2 to 0.33, which corresponds to molar ratios of M(II) to M(III) in the range from 2 to 4. Examples of divalent metals here include Mg, Fe, Ni, Co, Zn and Mn, examples of trivalent metals include Al, Ga, In, Co and Mn. The possibility of the simultaneous presence of a plurality of divalent or trivalent metals in different molar ratios increases the structural variety of the suitable hydrotalcites.

Merely by way of example, minerals of the hydrotalcite group include manasseite, pyroaurite, sjögrenite, stichtite, barbertonite, desautelsite, meixnerite or takovite, which are described in the literature and are known to those skilled in the art in terms of composition. A preferred hydrotalcite has the composition $Mg_6Al_2(CO_3)(OH)_{16} \times 4\ H_2O$.

Owing to its ability to bind acids by gradual release of aluminum hydroxide, hydrotalcite has various uses in industry and as a medicament.

Preferred variants of aluminum oxide are basic aluminum oxides or alumosilicates, as likewise known to those skilled in the art and described in the literature.

The supported catalysts used in accordance with the invention can be prepared by processes which are known per se to those skilled in the art and are described in the literature. For example, EP-A 172 565 or EP-A 357 292 describes a process for preparing supported silver catalysts, which, with appropriate adjustment, can also be used for the preparation of the catalysts of the present invention. Mention should also be made here of the preparation of the supported catalysts used in the process according to the invention via what is known as the flame spraying process (description of the technology, for example, in Army Engineering Manual EM 1110-2-3401) or else of a preparation based on the process described in *Angew. Chem. Int. Ed.* 2007, 47, 138-141.

Owing to the simpler mode of preparation, catalysts according to the process described in the last reference are preferred.

In the preparation, preferred in accordance with the invention, of 3-methylbut-2-en-1-al, the oxidative dehydrogenation is followed by subjecting the resulting reaction mixture of 3-methylbut-2-en-1-al and 3-methylbut-3-en-1-al to an isomerization under basic conditions in a manner known per se, in order to obtain the desired 3-methylbut-2-en-1-al end product. Corresponding processes for this purpose are known to those skilled in the art and described in the literature.

It has been found that, surprisingly, this above-described separate isomerization step can be dispensed with in the case of use of basic support materials as the support for the catalyst in the process according to the invention, since the desired 3-methylbut-2-en-1-al end product forms without a separate isomerization step in this case. Accordingly, such catalysts with basic support materials are used with preference in the process according to the invention.

The examples which follow constitute preferred embodiments of the process according to the invention and serve to further illustrate the invention.

EXAMPLE 1

Preparation of a supported catalyst on hydrotalcite as a support which is suitable for the process according to the invention.

In a 2000 mL round-bottom flask with overhead stirrer and reflux condenser, a solution of $MgCl_2 \times 6H_2O$ (31.2 g, 154 mmol) and $AlCl_3 \times 6H_2O$ (12.3 g, 51 mmol) in water (1000 mL) was added gradually at room temperature to a solution of NaOH (18.6 g, 465 mmol) and $Na_2CO_3$ (14.2 g, 134 mmol) in water (130 mL). Then the reaction mixture was stirred at 65° C. overnight. The residue was filtered, washed to neutrality with water and dried at 110° C.

In a 500 ml stirred flask with overhead stirrer and reflux condenser, hydrotalcite (3.98 g from the above reaction) was added gradually at room temperature to a solution of $AuCl_3$ (140 mg) in water (300 mL), and the mixture was stirred at 60° C. for 12 h. The residue was filtered, washed with water until the pH was neutral, and dried at room temperature for 12 h. The gold content of the catalyst thus obtained was 1.50% by weight.

EXAMPLE 2

Preparation of a Supported Catalyst on Aluminum Oxide as a Support

In a closed stirrer apparatus, auric acid (3.41 g) was dissolved in water (1000 mL) and stirred for 15-20 min. The solution was heated to 70° C. and the pH was adjusted with a 0.5N NaOH solution (86.5 g, 43.3 mmol) while stirring vigorously. Then $Al_2O_3$ (50 g) was added and the mixture was stirred at 70° C. for 1 h. The reaction solution was cooled, filtered and washed. The water was removed under reduced pressure, and the catalyst was dried and calcined. The gold content of the catalyst thus obtained is 0.98% by weight.

EXAMPLE 3

Oxidation of Isoprenol to Prenal by the Process According to the Invention

In a round-bottom flask with a reflux condenser, the catalyst (510 mg, 1.5% by weight of Au/hydrotalcite) was added to a solution of isoprenol (550 mg, 6.4 mmol) in p-xylene (25 mL), and the reaction was blanketed with air at 130° C. and stirred for 6 h. Filtration of the catalyst gave 16.8 g of a yellowish liquid of the following composition: 1.63% by weight of prenal (3-methylbut-2-en-1-al, 3.27 mmol), 1.42% by weight of isoprenol (2.79 mmol), corresponding to 56.4% conversion, 88.1% selectivity and 51.1% yield.

EXAMPLE 4

Preparation of Prenal with a Supported Catalyst Based on Aluminum Oxide

Under the above-described conditions, $Au/Al_2O_3$ (0.98% by weight, 5.12 g) and isoprenol (17.2 g, 198 mmol) were converted in p-xylene (80 mL) at 110° C. Filtration of the catalyst gave 92.5 g of a yellowish liquid of the following composition: 3.29% by weight of prenal (36.2 mmol), 14.3% by weight of isoprenol (157.3 mmol), corresponding to 21.3% conversion, 85.1% selectivity and 18.1% yield.

EXAMPLE 5

Conversion of a Mixture of Isoprenol/Prenol

In a glass autoclave, prenol (14.0 g, 162.5 mmol) and isoprenol (7.70 g, 89.4 mmol) were dissolved in o-xylene (90 ml), and the catalyst (2.40 g, 3.8% by weight of Pd, 3.1% by weight of Au on carbon, preparation analogous to description in Example 2) was added, 5 bar of air were injected and the gas phase was exchanged continuously (30 l/h) at 80° C. The mixture was stirred vigorously for 1 h. Removal of the catalyst and analysis of the residue gave the following composition: 8.78% by weight of prenal, 6.11% by weight of isoprenol, 5.67% by weight of prenol, corresponding to 47.8% conversion and 86.6% selectivity (prenal).

EXAMPLE 6

Conversion of a Mixture of Isoprenol/Prenol

In a glass autoclave, prenol (14.0 g, 162.5 mmol) and isoprenol (7.70 g, 89.4 mmol) were dissolved in o-xylene (90 ml), and the catalyst (2.40 g, 3.8% by weight of Pd, 3.1% by weight of Au on carbon, preparation analogous to description in Example 2) was added, 5 bar of air were injected and the gas phase was exchanged continuously (30 l/h) at 80° C. The mixture was stirred vigorously for 2 h. Removal of the catalyst and analysis of the residue gave the following composition: 10.8% by weight of prenal, 4.6% by weight of isoprenol, 3.2% by weight of prenol, corresponding to 66.9% conversion and 76.6% selectivity (prenal).

EXAMPLE 7

Regeneration and Testing of the Catalyst from the Previous Example

The removed catalyst from the previous example was washed repeatedly with o-xylene and dried in a nitrogen stream at 100° C. overnight. The catalyst thus regenerated was used analogously to Example 6, and analysis of the reaction discharge gave the following composition: 10.4% by weight of prenal, 4.7% by weight of isoprenol, 2.9% by weight of prenol, corresponding to 62.7% conversion and 72.8% selectivity (prenal).

The invention claimed is:
1. A process for preparing olefinically unsaturated carbonyl compounds of the formula I

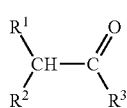

where $R^1$ is hydrogen when $R^2$ is a radical of the formula II

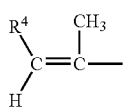

or $R^1$ and $R^2$ together are a radical of the formula III

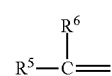

where $R^3$, $R^4$, $R^5$ and $R^6$ are each independently hydrogen, a $C_1$-$C_{18}$-alkyl group, an optionally substituted $C_5$-$C_{18}$-cycloalkyl group or an optionally substituted $C_6$-$C_{18}$-aryl group, and some of the ring atoms of the cycloalkyl and aryl groups are optionally replaced by heteroatoms selected from N, O and S,
which comprises converting alcohols of the formula IV

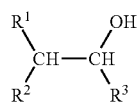

wherein $R^1$, $R^2$ and $R^3$ are each as defined above,
by oxidative dehydrogenation in an oxygenous atmosphere over a gold catalyst, which comprises using, as the gold catalyst, a supported catalyst which comprises gold or a mixture of gold and noble metals selected from Cu, Ag, Pd, Pt, Rh, Ru, W and Os, the conversion being performed at temperatures in the range from 50 to 240° C. and in the presence of air, hydrogen peroxide or a gas or gas mixture with an oxygen content in the range from 7 to 30% by volume as the oxygenous atmosphere and wherein the support material used is aluminum oxide, an aluminosilicate or a hydrotalcite or mixtures thereof.

2. The process according to claim 1, wherein the conversion is performed at a temperature in the range from 80 to 200° C.

3. The process according to claim 2, wherein the conversion is performed at a temperature in the range from 100 to 150° C.

4. The process according to claim 1, wherein the alcohol of the formula IV used is 3-methylbut-3-en-1-ol.

5. The process according claim 1, wherein the alcohol used is a mixture of 3-methylbut-3-en-1-ol and 3-methylbut-2-en-1-ol.

6. The process according to claim 4, wherein 3-methylbut-3-en-1-al still present in the reaction products is isomerized to 3-methylbut-2-en-1-al.

7. A process for preparing olefinically unsaturated carbonyl compounds of the formula I

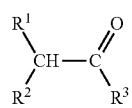

where $R^1$ is hydrogen when $R^2$ is a radical of the formula II

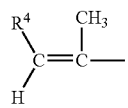

or $R^1$ and $R^2$ together are a radical of the formula III

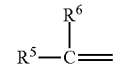

where $R^3$, $R^4$, $R^5$ and $R^6$ are each independently hydrogen, a $C_1$-$C_{18}$-alkyl group, an optionally substituted $C_5$-$C_{18}$-cycloalkyl group or an optionally substituted $C_6$-$C_{18}$-aryl group, and some of the ring atoms of the cycloalkyl and aryl groups are optionally replaced by heteroatoms selected from N, O and S,
which comprises adding alcohols of the formula IV

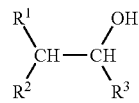

wherein $R^1$, $R^2$ and $R^3$ are each as defined above,
in the presence of air, hydrogen peroxide or a gas or gas mixture with an oxygen content of 7 to 30% by volume at temperatures in the range from 50 to 240° C. which comprises utilizing a supported catalyst which comprises gold or a mixture of gold with further noble metals selected from Cu, Ag, Pd, Pt, Rh, Ru, W and Os as a catalytically active species and wherein the support material used is aluminum oxide, an aluminosilicate or a hydrotalcite or mixtures thereof.

8. The process according claim 1, wherein the temperature range is from 100 to 200° C.

9. The process according claim 1, wherein the temperature range is from 100 to 150° C.

10. The process according claim 7, wherein the temperature range is from 100 to 200° C.

11. The process according claim 7, wherein the temperature range is from 100 to 150° C.

12. The process according claim 1, wherein the oxygen content is form 9 to 18% by volume.

13. The process according claim 7, wherein the oxygen content is form 9 to 18% by volume.

* * * * *